US010383683B2

(12) United States Patent
Ogata et al.

(10) Patent No.: US 10,383,683 B2
(45) Date of Patent: Aug. 20, 2019

(54) REDIRECTING DELIVERY CATHETER AND METHODS OF USE THEREOF (71) Applicant: Asahi Medical Technologies, Inc., Pleasanton, CA (US)

(72) Inventors: Wayne Ogata, San Ramon, CA (US); Steven Meyer, Oakland, CA (US); Xiang Ian Gu, Foster City, CA (US)

(73) Assignee: ASAHI MEDICAL TECHNOLOGIES, INC., Pleasanton, CA (US)

( * ) Notice: Subject to any disclaimer, the term of this patent is extended or adjusted under 35 U.S.C. 154(b) by 376 days.

(21) Appl. No.: 14/887,940

(22) Filed: Oct. 20, 2015

(65) Prior Publication Data
US 2016/0106499 A1 Apr. 21, 2016

Related U.S. Application Data (60) Provisional application No. 62/066,311, filed on Oct. 20, 2014.

(51) Int. Cl.
*A61B 17/00* (2006.01)
*A61B 17/22* (2006.01)
(Continued)

(52) U.S. Cl.
CPC ...... *A61B 18/1492* (2013.01); *A61B 17/3207* (2013.01); *A61M 25/0074* (2013.01);
(Continued)

(58) Field of Classification Search
CPC ...... A61B 17/3207; A61B 2017/00876; A61B 2017/22001; A61B 2017/22042;
(Continued)

(56) References Cited

U.S. PATENT DOCUMENTS 4,552,554 A 11/1985 Gould
5,366,443 A 11/1994 Eggers et al.
(Continued)

FOREIGN PATENT DOCUMENTS

WO 01/49187 A1 7/2001

OTHER PUBLICATIONS

International Preliminary Report on Patentability for corresponding PCT Application No. PCT/IB2015/002386 dated Apr. 25, 2017.
International Search Report for International Patent Application No. PCT/IB15/02386 (dated May 6, 2016).
(Continued)

*Primary Examiner* — Ronald Hupczey, Jr.
(74) *Attorney, Agent, or Firm* — Pepper Hamilton LLP (57) ABSTRACT

A redirecting delivery catheter includes a first longitudinal member having an inner chamber configured to receive a second longitudinal member, an outer surface surrounding the inner chamber, a first region located at a proximal end, a second region located at a distal end, and a length. An opening in the outer surface extends along a portion of the length of the first longitudinal member between the first region and the second region. A deflecting mechanism is located proximate to the opening and is configured to be capable of transforming from a first position to a second position. The deflecting mechanism is configured to enable the second longitudinal member to access the second region in the second position and to deflect the second longitudinal member towards the opening in the first position. Methods of use of the redirecting delivery catheter are also disclosed.

25 Claims, 7 Drawing Sheets

(51) Int. Cl.
  *A61B 18/00* (2006.01)
  *A61B 18/14* (2006.01)
  *A61B 18/18* (2006.01)
  *A61M 25/00* (2006.01)
  *A61M 25/09* (2006.01)
  *A61B 17/3207* (2006.01)

(52) U.S. Cl.
  CPC .......... *A61M 25/09041* (2013.01); *A61B 2017/00876* (2013.01); *A61B 2017/22001* (2013.01); *A61B 2017/22042* (2013.01); *A61B 2017/22044* (2013.01); *A61B 2017/22094* (2013.01); *A61B 2017/22095* (2013.01); *A61B 2018/0022* (2013.01); *A61B 2018/00345* (2013.01); *A61B 2018/00577* (2013.01); *A61B 2018/144* (2013.01); *A61B 2018/1435* (2013.01); *A61B 2018/1475* (2013.01); *A61B 2018/1861* (2013.01); *A61M 25/0075* (2013.01); *A61M 2025/0076* (2013.01); *A61M 2025/0079* (2013.01)

(58) Field of Classification Search
  CPC ........... A61B 2017/22044; A61B 2017/22094; A61B 2017/22095; A61B 18/1492; A61B 2018/00876; A61B 2018/0022; A61B 2018/00345; A61B 2018/00577; A61B 2018/1861; A61M 25/0074; A61M 25/09041; A61M 25/0075; A61M 25/2025; A61M 25/0076; A61M 25/0079
  See application file for complete search history.

(56) References Cited

U.S. PATENT DOCUMENTS

| | | |
|---|---|---|
| 5,419,767 A | 5/1995 | Eggers et al. |
| 5,514,128 A | 5/1996 | Hillsman et al. |
| 6,183,432 B1 | 2/2001 | Milo |
| 6,416,523 B1 | 7/2002 | Lafontaine |
| 6,585,650 B1 | 7/2003 | Solem |
| 6,911,026 B1 | 6/2005 | Hall et al. |
| 2003/0032936 A1 | 2/2003 | Lederman |
| 2003/0195495 A1* | 10/2003 | Ryan ............ A61B 18/1492 606/15 |
| 2004/0267251 A1 | 12/2004 | Sutton |
| 2006/0047222 A1 | 3/2006 | Heuser |
| 2006/0047335 A1 | 3/2006 | Israel |
| 2008/0188804 A1* | 8/2008 | Jordan ............ A61F 2/95 604/103.04 |
| 2009/0264780 A1* | 10/2009 | Schilling ............ A61N 1/057 600/509 |
| 2010/0191151 A1* | 7/2010 | Kwak ............ A61B 18/1492 600/585 |
| 2013/0006167 A1 | 1/2013 | Alvarez et al. |
| 2013/0030447 A1* | 1/2013 | Adams ............ A61B 17/2202 606/128 |
| 2014/0074108 A1 | 3/2014 | Warren |
| 2014/0330328 A1* | 11/2014 | Christie ............ A61N 1/3962 607/4 |

OTHER PUBLICATIONS

European Search Report for EP Patent Application No. 15851891.0, dated Mar. 16, 2018, pp. 1-6.

* cited by examiner

REDIRECTING DELIVERY CATHETER AND METHODS OF USE THEREOF

This application claims the benefit of U.S. Provisional Patent Application Ser. No. 62/066,311 filed Oct. 20, 2014, which is hereby incorporated by reference in its entirety.

FIELD

This technology relates to a redirecting delivery catheter, a recanalization system including the redirecting delivery catheter, and methods of use thereof for crossing severe or total chronic occlusions of lumens in the body.

BACKGROUND

Chronic total occlusion (CTO) is the complete blockage of a vessel and may have serious consequences if not treated in a timely fashion. The blockage could be due to atheromatous plaque or old thrombus. One of the common procedures for treating CTOs of the coronary arteries is percutaneous transluminal coronary angioplasty (PTCA).

During a PTCA procedure, a small incision is typically made in the groin. A guiding catheter over a guidewire is introduced into the femoral artery and advanced to the occlusion. At times, with gentle maneuvering, the guidewire is able to cross the occlusion. A balloon-tipped angioplasty catheter is then advanced over the guidewire to the occlusion. The balloon is inflated, separating or fracturing the atheroma. Often times, a stent is subsequently or simultaneously deployed.

Some of the common steps involved in the PTCA procedure for CTOs are the simultaneous injection of a contrast agent in the contra-lateral vessel, securing backup force or stabilization for a guidewire (which could invoke additional personnel to handle the catheter), puncturing the plaque, drilling or rotating the guidewire to push it through the dense plaque, etc. Because of the stiff resistance sometimes offered by dense plaque, one could be forced to use stiff wires. Occasionally, the wires could puncture the vessel wall calling for remedial measures.

The most common percutaneous coronary intervention (PCI) failure mode for CTOs is inability to successfully pass a guidewire across the lesion into the true lumen of the distal vessel. To date, there is no consensus on how best to treat CTO after attempts with conventional guidewires have failed. Different strategies for CTOs have been developed including the side branch technique, the parallel wire technique, and the IVUS guided technique. Mechanical and energy based devices have also been proposed for passing guidewires through hard calcified occlusions, such as mechanical cutting or oscillation and laser or ultrasound or radiofrequency (RF) energy ablation. Each of these devices works by strictly utilizing an antegrade approach and locally applying energy (typically in the form of heat) at the tip of the guidewire or catheter device in order to create a channel and hopefully enter the distal true lumen.

RF energy is widely used to coagulate, cut, or ablate tissue. In both monopolar and bipolar modalities, conductive electrodes contact the tissue to be treated. For the monopolar mode, the active electrode is placed in contact with the tissue to be treated and a return electrode with a large surface area is located on the patient at a distance from the active electrode. In the bipolar mode, the active and return electrodes are in close proximity to each other bracketing the tissue to be treated. Sometimes an array of electrodes is used to provide better control over the depth of penetration of the RF field and hence control over the temperatures to which the tissue is heated.

There are a number of disadvantages with both the monopolar and bipolar modalities. For example, in the monopolar arrangement, because of the large physical separation between the electrodes there are frequent reports of local burning at the electrode sites. This would clearly be undesirable where one of the electrodes will be inside a blood vessel. The other serious issue is the likelihood of forming blood clots. The tissue that is in contact with the electrodes can be coagulated or ablated. In the case of the electrodes being present inside a blood vessel, the formation of dangerous blood clots would obviously be undesirable.

In an attempt to overcome the issues described above, device and electrode configurations are described, for example, in U.S. Pat. Nos. 5,366,443 and 5,419,767 to Eggars et al. which describe the use of RF electrodes on a catheter to cross a lesion. These patents describe a bipolar electrode assembly at the distal tip of a catheter that is in contact with the occlusion, and patentees claim that application of RF energy ablates the occlusion and renders the occlusion susceptible for the guidewire to penetrate. This method has the drawback that careful tracking of the occlusion and the ablation process is necessary to avoid trauma to the vessel walls or healthy tissue, since the possibility of short-circuiting of current through healthy tissue instead of the occlusion is high. U.S. Pat. No. 5,419,767 to Eggars et al. overcomes this limitation to a certain extent through the use of a multiple electrode array. However, this device requires a channel to be pre-created through the occlusion so that the device can be passed through a guidewire traversing this channel, which is not always easy.

U.S. Pat. No. 5,514,128 to Hillsman et al. describes a laser catheter device that enables ablation of an occlusion in the vasculature. This system has similar drawbacks to the ones described above, such as the need for a guidance system, potential for healthy tissue to be ablated, and complexity (and hence cost) of the device, etc.

One major problem with the existing devices is the potential for the ablation energy to damage the walls of the vasculature in the absence of a mechanism to track the orientation and position of the energy delivery member. Several devices exist in the prior art that address the issue of tracking and steering of the energy delivery element. U.S. Pat. No. 6,911,026 to Hall et al. describes a magnetic steering and guidance system to direct an ablation device that delivers RF energy at the tip in a unipolar configuration where the return electrode is placed externally in contact with the body or in a bipolar configuration where the return electrode is a ring surrounding the central wire electrode. U.S. Pat. No. 6,416,523 to Lafontaine discusses a mechanical cutting device where the guidance is provided by measuring impedance of the tissue in contact. The guidance system senses the difference in impedance between the stenotic tissue and the vessel wall and directs the cutting element to the occlusion.

However, none of these alternate strategies have provided satisfactory results for the most challenging of the CTOs. Therefore, there is a need for improved methods of ablating or disrupting the occlusive material that are safe, efficacious, and fast. It would be beneficial to have alternate techniques and devices that would recanalize a CTO without the shortcomings of the current techniques.

CTOs that are hard to recanalize, either because the proximal end of the stenosis is difficult to penetrate or because it is difficult to access the distal true lumen, or other characteristics of the CTO that would make the standard procedure vulnerable to failure would benefit from newer approaches to recanalize CTOs. Recently a combined antegrade-retrograde approach has been proposed for recanalizing chronic occlusions (U.S. application Ser. No. 11/706, 041). The method disclosed in the co-pending application would benefit from the use of energy for crossing CTOs.

SUMMARY

A redirecting delivery catheter includes a hollow longitudinal member configured to accommodate a second longitudinal member. The hollow longitudinal member has a first region located at a proximal end, a second region located at a distal end, and a length. An opening extends along a portion of the length of the hollow longitudinal member between the first region and the second region. A deflecting mechanism is located proximate to the opening and is configured to be capable of transforming from a first position to a second position. The deflecting mechanism is configured to enable the second longitudinal member to access the second region when the deflecting mechanism is in the second position and to deflect the second longitudinal member toward the opening when the deflecting mechanism is engaged in the first position.

A recanalization system includes a guidewire and a redirecting delivery catheter. The redirecting delivery catheter includes a hollow longitudinal member configured to accommodate a second longitudinal member. The hollow longitudinal member has a first region located at a proximal end, a second region located at a distal end, and a length. An opening extends along a portion of the length of the hollow longitudinal member between the first region and the second region. A deflecting mechanism is located proximate to the opening and is configured to be capable of transforming from a first position to a second position. The deflecting mechanism is configured to enable the second longitudinal member to access the second region when the deflecting mechanism is in the second position and to deflect the second longitudinal member toward the opening when the deflecting mechanism is engaged in the first position.

A method of redirecting a guidewire includes inserting the guidewire into a lumen of a patient. A redirecting delivery catheter is advanced over the guidewire. The redirecting delivery catheter includes a hollow longitudinal member configured to accommodate a second longitudinal member. The hollow longitudinal member has a first region located at a proximal end, a second region located at a distal end, and a length. An opening extends along a portion of the length of the hollow longitudinal member between the first region and the second region. A deflecting mechanism is located proximate to the opening and is configured to be capable of transforming from a first position to a second position. The deflecting mechanism is configured to enable the second longitudinal member to access the second region when the deflecting mechanism is in the second position and to deflect the second longitudinal member toward the opening when the deflecting mechanism is engaged in the first position. The guidewire is retracted into the first region to transform the deflecting mechanism from the first position to the second position. The guidewire is advanced toward the deflecting mechanism to redirect the guidewire toward the opening.

The present technology provides a number of advantages including enabling safer and more effective energy delivery using a longitudinal member through or around the occlusion by redirecting the longitudinal member. Additionally, the same catheter may be configured to enable energy delivery via a longitudinal member from a secondary position such as a subintimal space to deliver energy for recanalization therapy.

BRIEF DESCRIPTION OF THE DRAWINGS

FIGS. 1A-1C are side perspective phantom views of an example of a recanalization system including a redirecting delivery catheter with an exemplary deflection mechanism and a guidewire positioned at various locations within the redirecting delivery catheter.

DETAILED DESCRIPTION

Figure 1A:
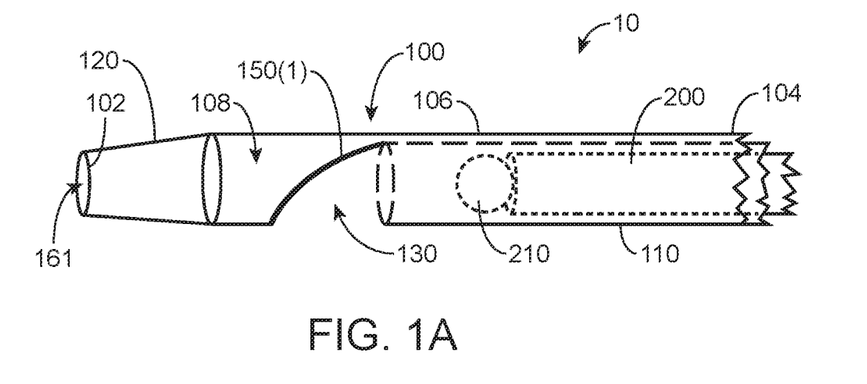
Figure 1B:
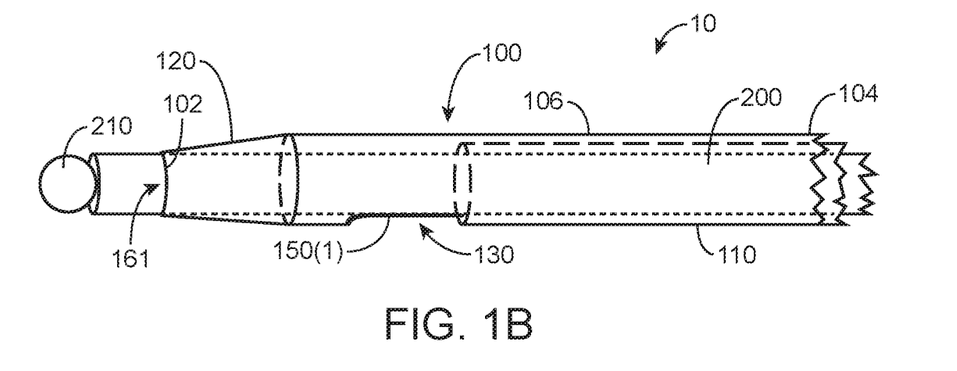
FIG. 1B shows the example of the recanalization system in FIG. 1A with the guidewire extending beyond a distal end of the redirecting delivery catheter.
Figure 1C:
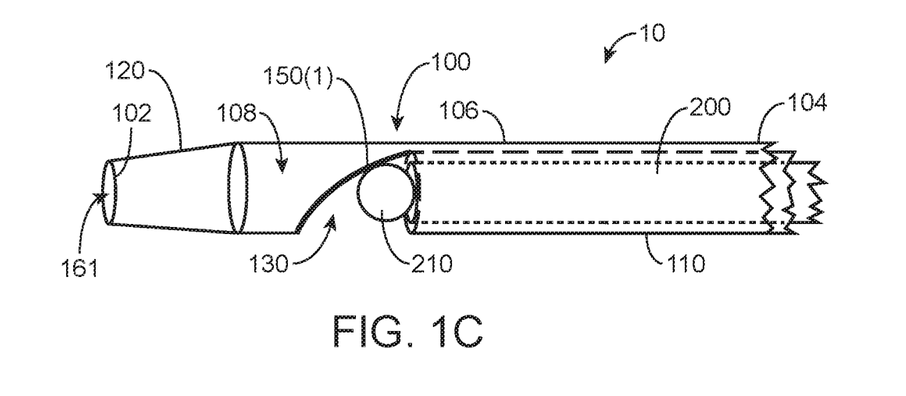
FIG. 1C shows the example of the recanalization system in FIG. 1A with the guidewire placed at the window region.

An exemplary recanalization system 10 is illustrated in FIGS. 1A-1C. The recanalization system 10 includes a redirecting delivery catheter 100 and a guidewire 200, although the recanalization system may include other types and numbers of devices, components, and/or other elements in other configurations, including, by way of example only, additional guidewires. By way of example, two guidewires or other longitudinal members may be used in an antegrade/retrograde configuration where one of the longitudinal members is configured to serve as an antegrade member and another longitudinal member is configured to serve as a retrograde member. This exemplary technology provides a number of advantages including providing a system that allows for recanalization of chronic total occlusions. Additionally, the exemplary system advantageously allows for redirecting a guidewire inserted into a vessel to access the lumen from a lateral direction, while at the same time limiting the amount of lateral force applied in accessing the lumen.

Figure 2:
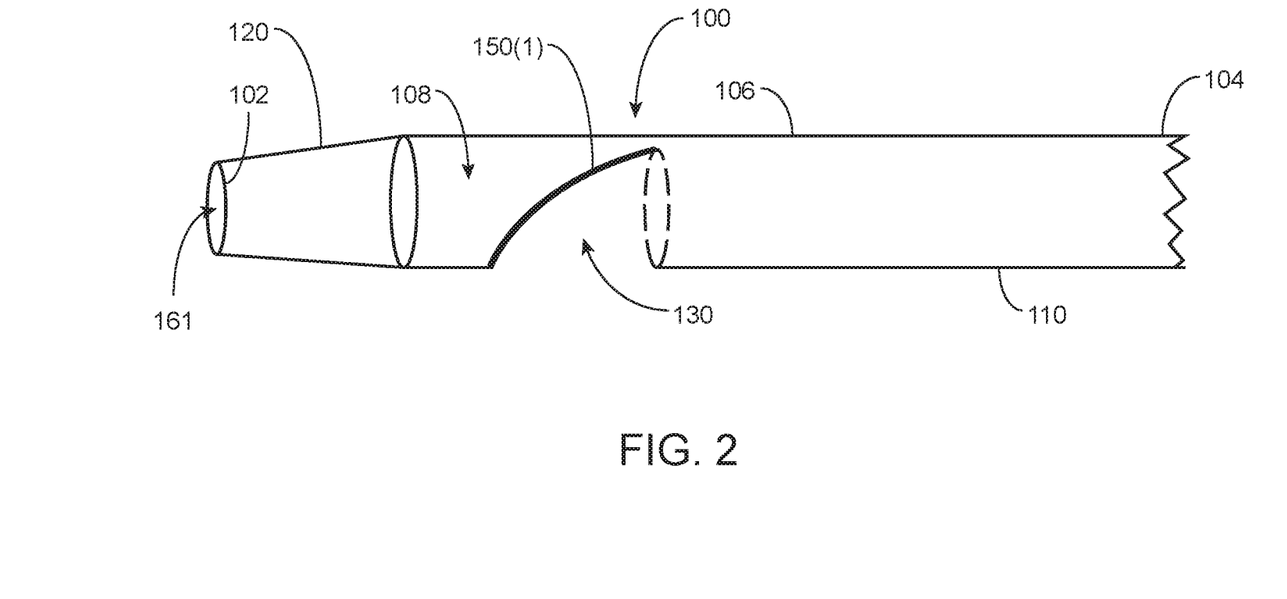
FIG. 2 is a side perspective phantom view of the redirecting delivery catheter shown in FIGS. 1A-1C.

Referring more specifically now to FIG. 2, the exemplary redirecting delivery catheter 100 is illustrated. The redirecting delivery catheter 100 includes a distal end 102, a proximal end 104, an outer surface 106, an inner chamber 108, a first region 110, a second region 120, an opening 130, and a deflecting mechanism 150(1), although the redirecting delivery catheter may include other types and numbers of components, and/or other elements in other configurations.

The redirecting delivery catheter 100 extends as a longitudinal member along a length between the distal end 102 and the proximal end 104 with the cylindrical outer surface 106, although outer surface 106 may have other shapes such as oval or flat (eccentric). The redirecting delivery catheter 100 may have any length known in the art for catheters. In one example, the cylindrical outer surface defines the cylindrical inner chamber 108 that is configured to accommodate a second longitudinal member, such as a guidewire, although the redirecting delivery catheter 100 may have other layers inside the outer surface 106 that form the inner chamber 108.

The first region 110 and the second region 120 of the redirecting delivery catheter 100 are defined by the positioning of the opening 130, although the redirecting delivery catheter 100 may have other numbers of regions defined in other manners. In this example, the first region 110 extends between the proximal end 104 of the redirecting delivery catheter 100 and the opening 130, while the second region 120 extends between the distal end 102 of the redirecting delivery catheter 100 and the opening 130. Further, in this example the distal end 102 of the redirecting delivery catheter 100 has a tapered configuration with the diameter of a distal opening 161 configured to be smaller than the diameter of the second region 120 near the opening 130 of the redirecting delivery catheter 100, although the distal end 102 may have other configurations. In one example, the first region 110 and/or the second region 120 has a helical exterior, although other configurations may be utilized. The first region 110 and the second region 120 may further comprise a plurality of wires that serve as conductive wires. In one example, the plurality of wires may have different diameters.

The opening 130 extends along a portion of the outer surface 106 of the redirecting delivery catheter 100, such that the opening 130 is positioned in a direction lateral to the distal opening 161. The opening 130 may have various lengths along the outer surface 106 depending on the application. As shown in FIG. 2, the opening 130 is configured as a flat opening in the outer surface 106.

In this example, the deflecting mechanism 150(1) is located near the opening 130. The deflecting mechanism 150(1) is shown in FIG. 2 in its default position. Referring now to FIGS. 1A-1C, the deflecting mechanism 150(1) provides a first position as shown, by way of example, in FIGS. 1A and 1C, and a second position as shown, by way of example in FIG. 1B. In the first position, which in this example is the default position of the deflecting mechanism 150(1), the deflecting mechanism 150(1) prevents access of a second longitudinal member, such as guidewire 200 inserted into the first region 110 along the inner chamber 108, to the second region 120 of the redirecting delivery catheter 100. In this example, the deflecting mechanism 150(1) has a substantially curved configuration in the first position, as shown in FIGS. 1A, 1C, and 2, in order to direct the guidewire 200 in direction lateral to the distal opening 161 of the redirecting delivery catheter when the guidewire is pushed toward the deflecting mechanism 150(1), although other configurations may be utilized. By way of example, the deflecting mechanism 150(1) may be a polymer tube capable of being compressed into the second position as shown in FIG. 1B. In the second position, by way of example, the deflecting mechanism 150(1) is compressed to allow access of the guidewire 200 to the second region 120 of the redirecting delivery catheter 100 and to the distal opening 161.

Figure 3A:
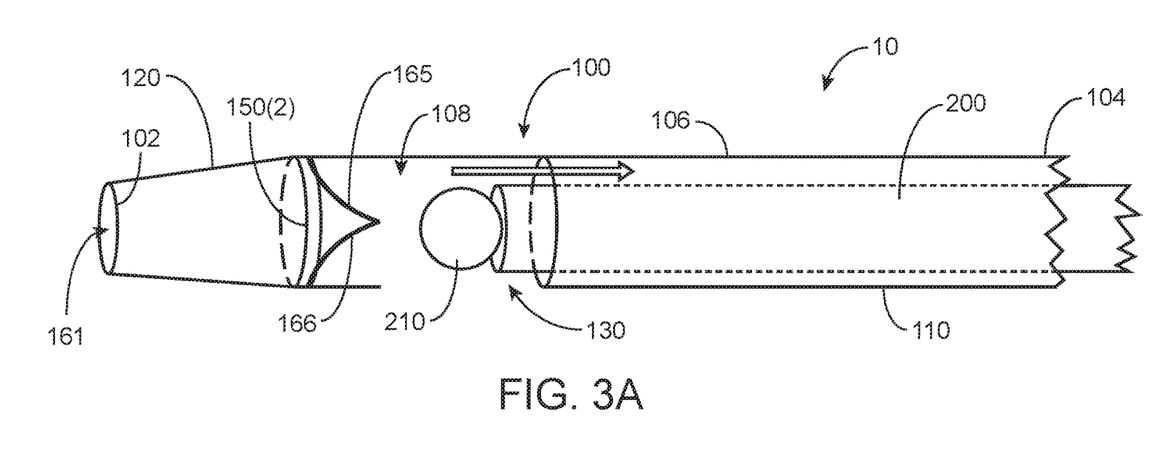
FIGS. 3A and 3B are side perspective phantom views of the recanalization system with another exemplary deflecting mechanism with the guidewire positioned at various locations within the redirecting delivery catheter.
Figure 3B:
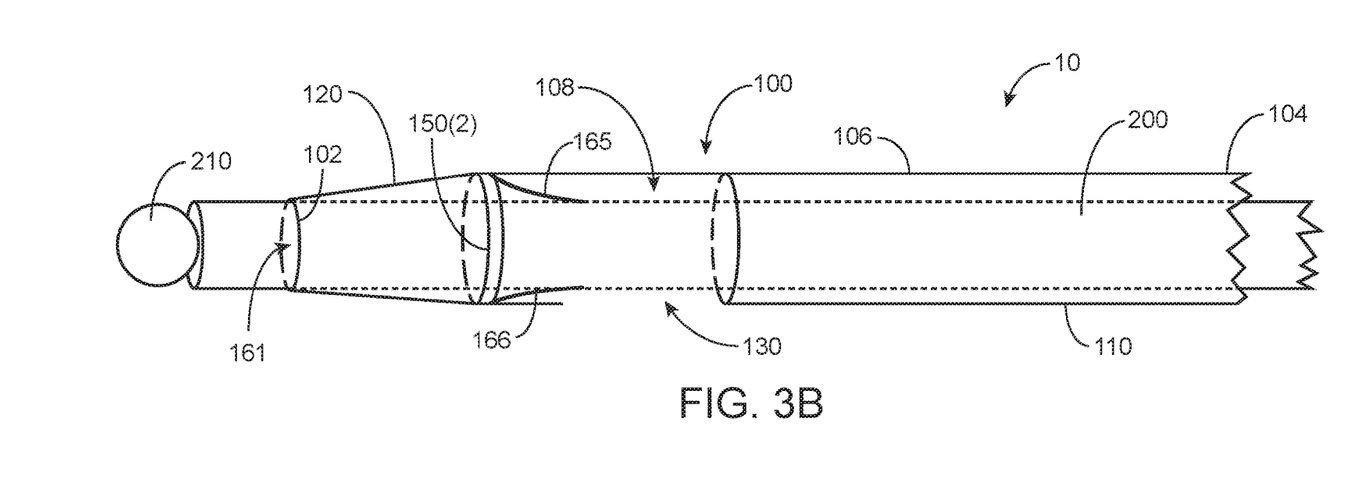

Another example of a recanalization system 10 including the redirecting delivery catheter 100 and the guidewire 200, where the redirecting delivery catheter 100 includes a deflecting mechanism 150(2), is shown in FIGS. 3A and 3B. The deflecting mechanism 150(2) is defined by two lips 165 and 166 that meet to form a one-way valve, although other numbers of lips or other structures may be utilized. The deflecting mechanism 150(2) may be constructed, by way of example, of a flexible polymer, although other materials may be utilized.

The deflecting mechanism 150(2) provides a first position, as shown in FIG. 3A, where the one-way valve prevents access of a second longitudinal member, such as guidewire 200 inserted into the first region 110 along the inner chamber 108, to the second region 120 of the redirecting delivery catheter 100. In this example, the deflecting mechanism 150(2) directs the guidewire 200 in direction lateral to the distal opening 161 of the redirecting delivery catheter when the guidewire is pushed toward the deflecting mechanism 150(2), although other configurations may be utilized. In the second position, as shown in FIG. 3B, each of the lips 165 and 166 of the deflecting mechanism 150(2) are compressed to allow access of the guidewire 200 to the second region 120 of the redirecting delivery catheter 100 and to the distal opening 161. The two lips 165 and 166 of the deflecting mechanism effectively seal the inner chamber 108 of the redirecting delivery catheter 100 between the first region 110 and the second region 120 when the lips 165 and 166 collapse on each other. Upon retracting the guidewire 200 from an initial position where the guidewire is at least partly within the second region 120 to the opening 130, the deflecting mechanism 150(2) effectively prevents the guidewire 200 from re-entering into the second region 120. In yet another example, the deflecting mechanism comprises a membrane covering that can be penetrated by the guidewire, although said membrane is configured to create a resistance such that sufficient force must be applied to overcome the resistance in order to traverse the membrane.

Figure 4:
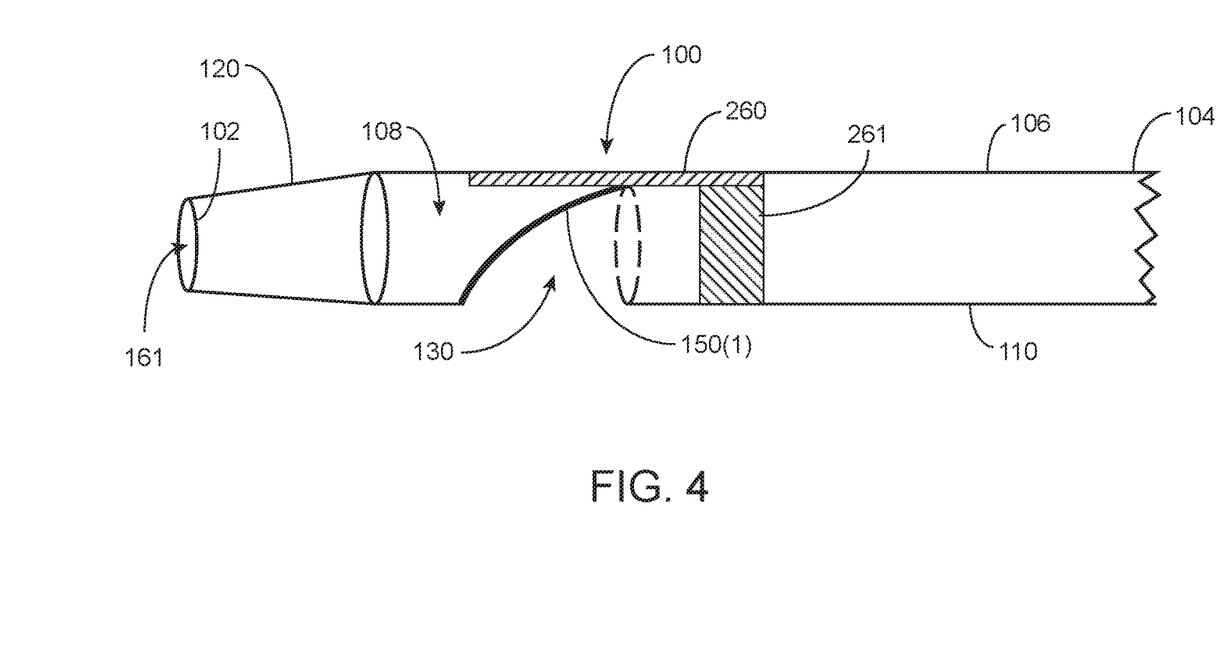
FIG. 4 shows an example of a redirecting delivery catheter with radiopaque markers proximal to the opening.

The redirecting delivery element or catheter may comprise additional or optional components. As shown in FIG. 4, the redirecting delivery catheter 100 may comprise multiple radiopaque markers to help determine the orientation of the catheter relative to the lumen of the vessel. By way of example only, the redirecting delivery catheter 100 may have an orientation marker 260 placed at a location opposite the opening 130 that serves to orient the opening 130 towards the lumen and away from the vessel wall. The redirecting delivery catheter 100 may further include a second marker 261 that serves to allow for approximate location of the window. Although two markers 260 and 261 are shown in FIG. 4, in another example, the redirecting delivery catheter 100 may include a single radiopaque marker in a single L-shaped configuration.

Figure 5A:
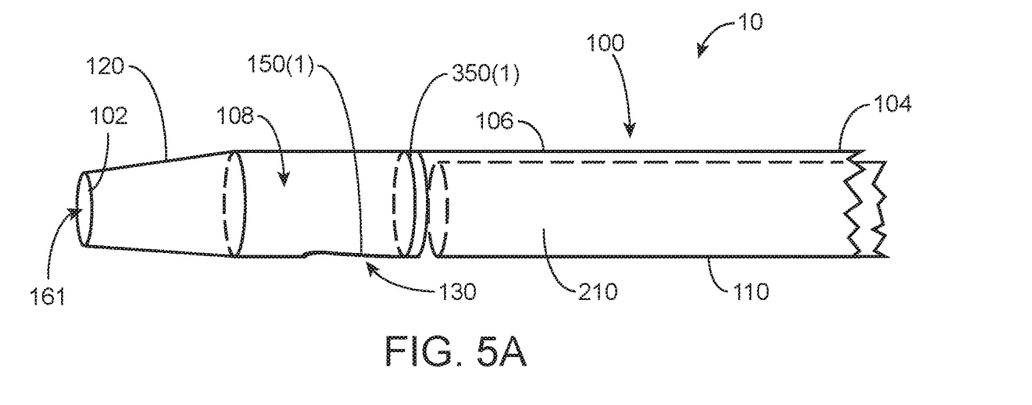
FIG. 5A shows an example of a redirecting delivery catheter comprising a support element while in a first position.
Figure 5B:
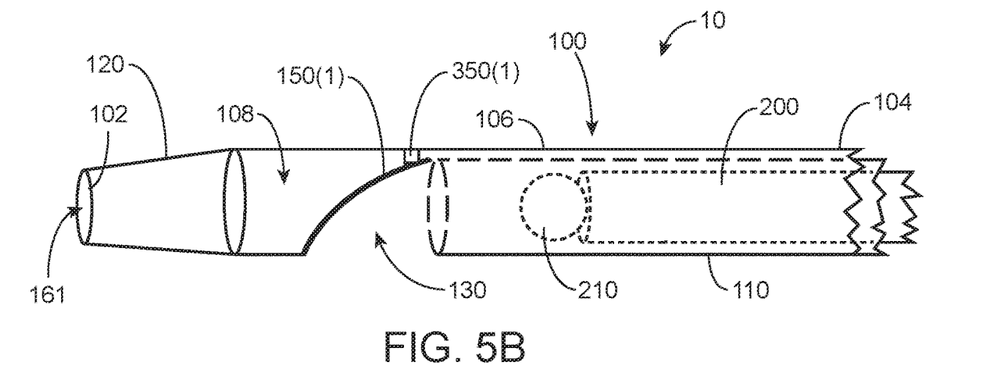
FIG. 5B shows the redirecting delivery catheter shown in FIG. 5A with the support element in a semi-circular configuration while in a second position.
Figure 5C:
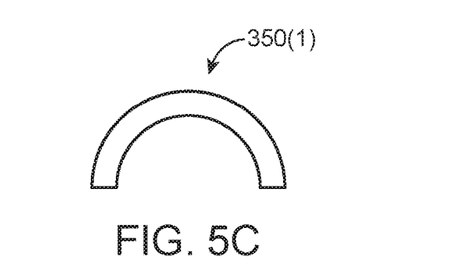
FIG. 5C shows a cross section of the example of the support element as shown in FIG. 5B.

In one example, as shown in FIGS. 5A-5C, the redirecting delivery catheter 100 further includes an optional support element 350(1) may be included to support the integrity to the deflecting mechanism 150(1), by way of example, in moving from a first position (with the opening 130 open) to a second position (with the opening 130 closed). In this example, the support element 350(1) is a circular ring that extends around the inner chamber 108 when the deflecting mechanism 150(1) is compressed to close the opening 130 as shown in FIG. 5A. The support member 350(1) is compressible to form a semicircular ring, as shown in FIGS.

5B and 5C, when the deflecting mechanism 150(1) is extended across the inner chamber 108 with the opening 130 unobstructed. The support element 350(1) may be constructed of a polymer or a shape memory material such as nitinol, although the support element 350(1) may be constructed of other biocompatible materials.

Figure 6A:
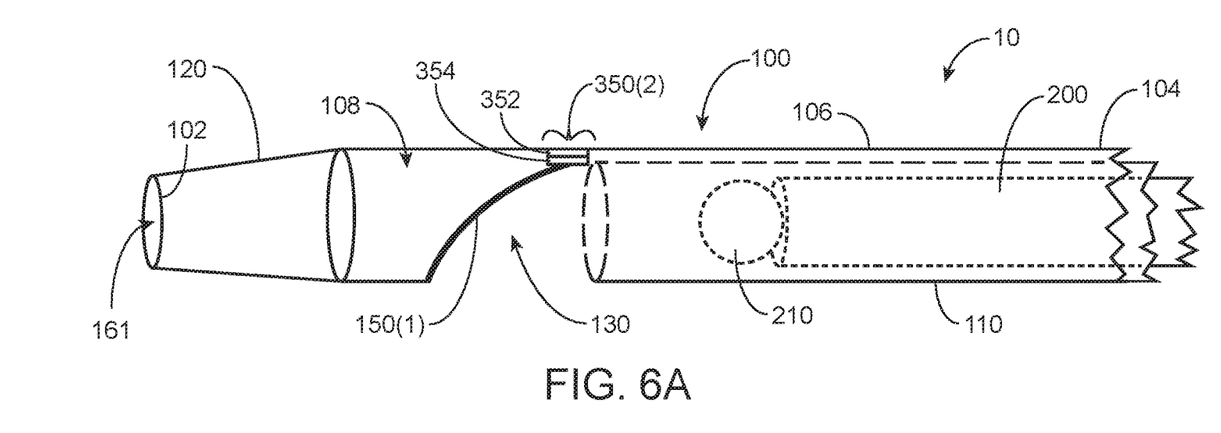
FIGS. 6A and 6B are side perspective phantom views of an example of a recanalization system including a pair of magnets and a guidewire positioned at various locations within the redirecting delivery catheter.
Figure 6B:
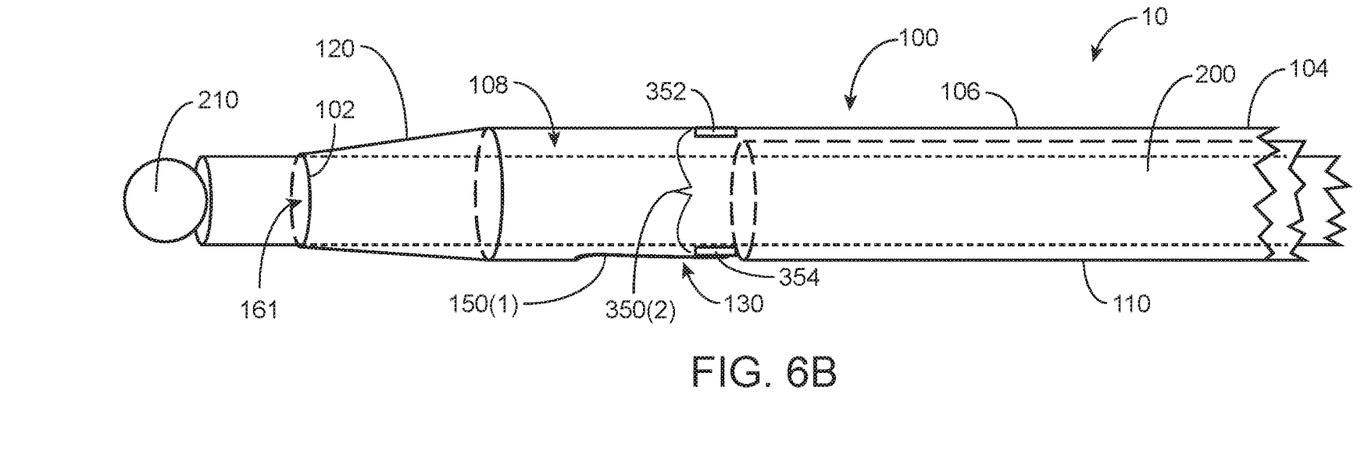

In another example, as shown in FIGS. 6A and 6B the redirecting delivery catheter 100 includes an optional support element 350(2) for supporting the integrity of the deflecting mechanism 150(1) that includes a pair of magnets 352 and 354 with opposite polarity. Alternatively, the pair of magnets 352 and 354 may serve as the deflecting mechanism themselves. In this example, when the guidewire 200 occupies the first region 110 and the second region 120, contact between the magnets 352 and 354 is prevented by the guidewire 200 as shown in FIG. 6B. Upon retraction of the guidewire 200, the magnets 352 and 354 are no longer obstructed by the guidewire 200 and are able to make contact, thus compressing the deflecting mechanism 150(1) and transforming the deflecting mechanism 150(1) to a closed position with respect to the inner chamber 108 as shown in FIG. 6A.

Figure 7:
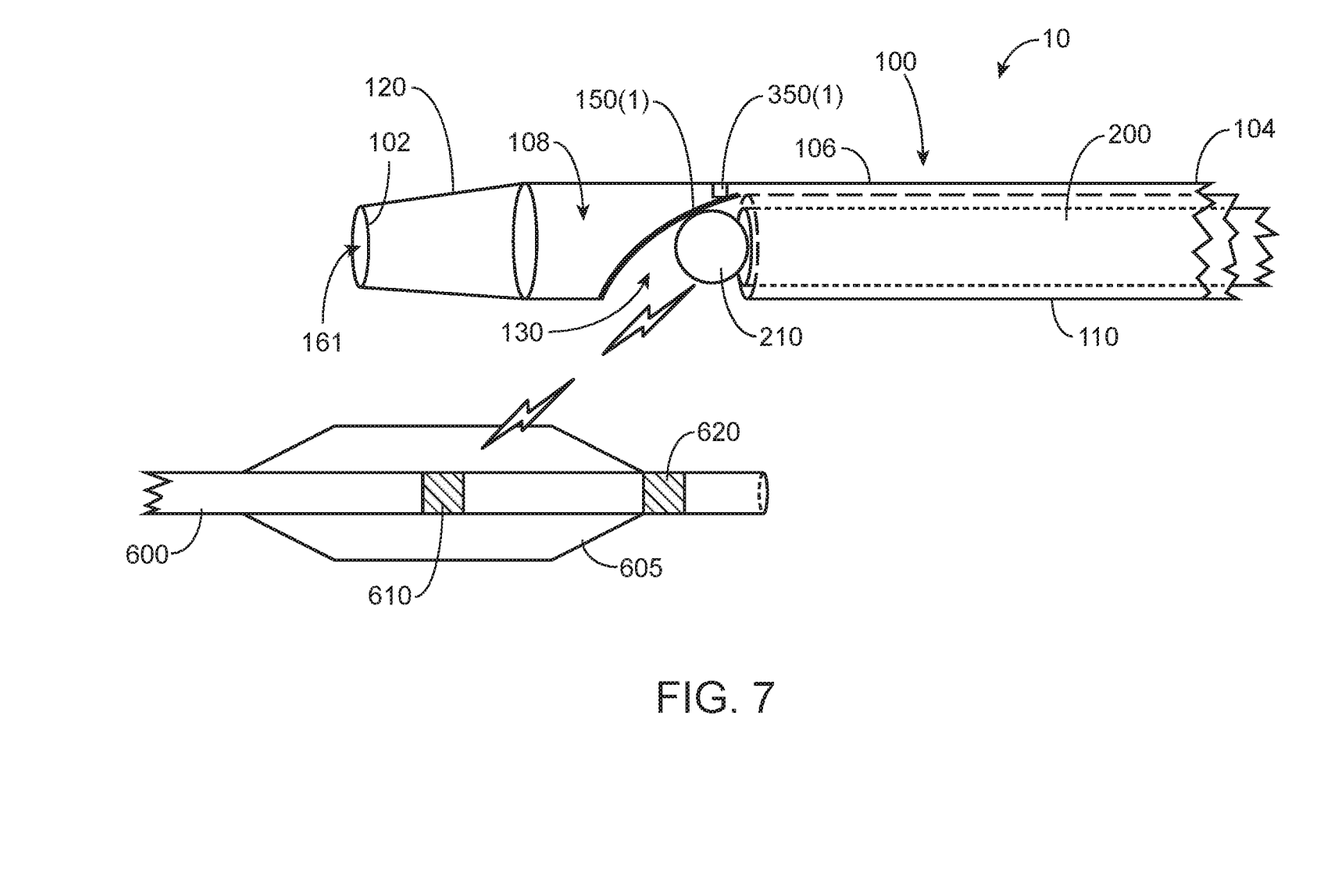
FIG. 7 shows another example of a redirecting delivery catheter system with one conductive electrode in the form of a guidewire and a second conductive electrode in the form of a balloon catheter.

The recanalization system 10 further includes the guidewire 200 or other longitudinal member, and may optionally include additional guidewires or other longitudinal members. By way of example, two guidewires or other longitudinal members may be used in an antegrade/retrograde configuration where one of the longitudinal members is configured to serve as an antegrade member and another longitudinal member is configured to serve as a retrograde member. In another example, the recanalization system 10 may include a second longitudinal member such as balloon catheter 600 with balloon 605 and a conductive electrode at either location 610 or location 620, as shown in FIG. 7. While the term "guidewire" is used to refer to a longitudinal member, it is to be understood that the term "guidewire" as used herein is intended to include any other type of longitudinal member including catheters, microcatheters, or dilating catheters.

In this example, the guidewire 200 includes a conductive electrode 210 located on a distal tip thereof, although the guidewire 200 may include any other number of conductive electrodes or other electrodes in other positions. By way of example, an electrode may be located on the side of the distal tip which directs the RF energy away from the vessel wall, thereby minimizing potential RF injury to the vessel wall.

An RF generator or controller (not shown) may serve as a source of RF energy to be provided to the longitudinal members, such as guidewire 200. Optionally, the RF generator may be a hand-held battery-operated device, although other types and numbers of RF generators may be utilized.

While the above example refers to the use of RF energy for the purpose of ablation, it should be noted that other energy modalities may be used as well, for example ultrasound energy. In one example, the one or more longitudinal members, such as guidewire 200 of the recanalization system 10 comprise one or more ultrasound transducers, instead of or in addition to RF electrodes. The ultrasound transducers provide ultrasound energy for ablating an occlusion. In one example, the antegrade and/or the retrograde longitudinal members may comprise ultrasound transducers and ablate the lesion from an antegrade as well as a retrograde direction, although other energy modalities could be utilized such as microwave and laser.

In some aspects, to provide energy, such as RF energy from a generator to the longitudinal members, such as guidewire 200, a pigtail connects at a proximal end 214 of the guidewire 200 to the RF generator and terminates at its distal end in a connector. The connector couples the input and output signals of the RF generator to the guidewire 200 and may take the form of a device similar to a torque device.

Referring again to FIG. 1A, the guidewire 200 is shown as positioned in the first region 110 of the redirecting delivery catheter 100. In FIG. 1B, the guidewire 200 is shown to be housed within the redirecting delivery catheter 100. The guidewire 200 is shown to have traversed the length of the first region 110, the opening 130, and the second region 120. A portion of the guidewire 200 including the conductive electrode 210 is shown to have traversed the distal opening 161 such that it would be exposed to a tissue region when implemented in a lumen of a patient. Referring now to FIG. 1C, the guidewire 200 is positioned such that the conductive electrode 210 is placed at the window 130. As previously described, in some aspects, the deflecting mechanism 150(1) is compressed in a default state. When the guidewire 200 is positioned in the redirecting delivery catheter 100 before the deflecting mechanism 150(1), the compressed configuration of the deflecting mechanism 150(1) creates a barrier that prevents the guidewire 200 from entering in to the second region 120, thus causing the guidewire 200 to be positioned at the opening 130.

An exemplary operation of the recanalization system 10 of the present technology will now be described with reference to FIGS. 1A-1C. The sequence of the recanalization treatment steps includes advancing the guidewire 200 into a vessel of a patient in an antegrade direction. The guidewire 200 may be advanced into an occlusion or subintimal space using standard angioplasty techniques.

The redirecting catheter 100 is then back loaded onto the guidewire 200 such that the guidewire is positioned as shown in FIG. 1B. Backloading the redirecting delivery catheter 100 onto the guidewire 200 causes the deflecting mechanism 150(1) to be compressed such that the guidewire 200 occupies the first region 110 and the second region 120 of the redirecting delivery catheter. The opening 130 of the redirecting delivery catheter is advanced to a position where the guidewire is to be redirected.

Once the location is confirmed, by way of example using radiopaque markers 260 and 261 as shown in FIG. 4, the guidewire 200 is retracted within the redirecting delivery catheter 100 past the deflecting mechanism 150(1) and into the first region 110, effectively decompressing the deflecting mechanism 150(1) and clearing access to the opening 130.

The guidewire 200 is then re-advanced toward the deflecting mechanism 150(1). The configuration of the deflecting mechanism, which in this example includes a curved shape as shown in FIG. 1C, deflects the guidewire 200 laterally toward the opening 130 to provide contact with the occlusion or tissue located outside the opening 130. The deflecting mechanism 150(1) in this position, which is the default position of the deflecting mechanism 150(1) effectively blocks access of the guidewire 200 to the first region In one example, a second guidewire or longitudinal member, such as balloon catheter 600 as shown in FIG. 7 is then advanced retrogradely towards the distal end of the occlusion and serves as the second conductive electrode 610/620 to create a bipolar arrangement, although the balloon catheter could also serve as the antegrade electrode with a separate guidewire providing the retrograde electrode. Energy treatment is then initiated. In another example, the second conductive electrode is also advanced in the antegrade direction into the occlusion or subintimal space.

Referring more specifically to FIG. 7, in one example, the second conductive electrode may be located on the balloon catheter 600. In this example, the balloon catheter 600 includes a second conductive electrode 610/620 that may be inside the balloon 605 (610) or outside the balloon 605 (620). As shown in FIG. 7, the first conductive electrode 210 is positioned in the subintimal space while the second conductive electrode 610/620 is located inside the balloon 605 (610) or within the blood vessel (620), respectively, or both. The second electrode 610 has the added benefit of centering the second electrode within the lumen thus facilitating the positioning of the electrically active regions with respect to the first electrode 210.

During operation, once an electrical connection is formed between the first conductive electrode 210 and the second conductive electrode 610/620, the resulting spark will cause the balloon 605 to rupture. This observable event (visible or audible), can act as a confirmation trigger letting the operator know that an electrical connection and likely a channel has been formed between the electrodes.

In some examples, the guidewires are advanced as deep into the occlusion as possible to minimize the distance between the electrodes and, consequently, minimize the length of the ablation zone. Confirmation that the guidewires are in an appropriate position can be generated by impedance measurements and/or by using any of the standard imaging techniques employed during interventional procedures, such as fluoroscopy or intravascular ultrasound (IVUS), in which transducers are placed on the distal ends of the guidewires.

The present technology may be utilized to combine the use of energy delivered through antegrade and retrograde members for recanalizing occluded lumens, particularly chronic total occlusions. The methods and systems described herein recanalize difficult to cross occlusions by taking advantage of an antegrade and retrograde approach to establish a bipolar electrode arrangement across the occlusion. This approach minimizes the potential of the vessel wall becoming perforated or injured, as may otherwise occur in a conventional bipolar RF treatment approach, where both RF electrodes are on the same side of the occlusion. Because the electrodes are distributed on opposite sides of the occlusion, the tissue that is ablated by the RF treatment (i.e., the occlusion) is well contained between the electrodes. This also allows the user to localize the treatment to the occlusion.

In the controlled antegrade and retrograde tracking (CART) technique the retrograde approach takes advantage of an intercoronary channel. Such a channel may be an epicardial channel, an inter-atrial channel, an intra-septal channel (also referred to as septal collateral), or a bypass graft. The basic concept of the CART technique is to create a channel through an occlusion, preferably with limited dissections, by approaching the occlusion both in the antegrade and retrograde directions.

While the combined antegrade and retrograde approach has been effective in crossing difficult to cross lesions, it has been observed that using energy, for example RF energy, to ablate or alter the tissue in a controlled fashion is beneficial in crossing hard to cross lesions. Such controlled energy deployment is achieved using a bipolar arrangement of the electrodes, where one electrode is located on the antegrade element and the other electrode that constitutes the bipolar arrangement is located on the retrograde element. These electrodes can also be referred to as the return and active electrodes. They are also referred to as the anode and cathode, respectively. The electrodes could also be arranged in an array (multiple electrodes), where the electrode arrangement provides better control over the depth of penetration of the RF field and thereby provides the ability to control the tissue temperature.

It should be noted that the combined antegrade and retrograde energy delivery techniques described above could also be used as an adjunct technique to crossing CTOs in combination with using conventional methods. The technique could be used to sufficiently soften or weaken the occlusion, thereby allowing a guidewire or catheter to cross the occlusion.

It should be noted that although the use of energy is described above, the redirecting delivery element 100 or catheter can also be used without the use of energy. In particular, when the guidewire 200 is positioned in the subintimal space, the redirecting delivery catheter 100 can be used to redirect a subsequent guidewire by deflecting the guidewire towards the lumen and away from the vessel wall. In one example, the subsequent guidewire comprises a sharp tip. In another example, the subsequent guidewire takes the form of a 3-dimensional distal tip. In this configuration, the 3-dimensional guidewire can be rotated rather than axially advanced to access the vessel lumen. This serves to reduce the lateral force placed on the subintimal space when a guidewire is advanced axially which can often lead to enlargement of the subintimal space. It should be noted that the use of energy similarly reduces the lateral force placed on the subintimal space.

In another aspect, the redirecting delivery element 100 or catheter can be used for treating bifurcations. In this aspect, the redirecting catheter 100 is advanced over the guidewire 200 into the main vessel until the opening 130 is located near the side branch. At this point, the guidewire 200 can be retracted until the deflecting mechanism 150(1) is activated and then the guidewire 200 is advanced through the opening 130 into the side branch. By using the single guidewire 200, the profile of the device and the number of guidewires used can be reduced.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A redirecting delivery catheter, comprising:
    a first longitudinal member having an inner chamber configured to receive a second longitudinal member, an outer surface surrounding the inner chamber, a first region located at a proximal end, a second region located at a distal end, and a length;
    an opening in the outer surface extending along a portion of the length of the first longitudinal member between the first region and the second region;
    a deflecting mechanism located proximate to the opening and configured to be capable of transforming from a first position to a second position, wherein the deflecting mechanism is configured to enable the second longitudinal member to access the second region when the deflecting mechanism is in the second position and to deflect the second longitudinal member toward the opening when the deflecting mechanism is in the first position; and a support element coupled to the deflecting mechanism to support the deflecting mechanism in transforming from the first position to the second position, wherein the support element comprises one of a compressible circular ring configured to extend at least partially around the inner chamber when the deflecting mechanism is in the second position and to compress to a semicircular configuration when the deflecting mechanism is in the first position or a first magnet positioned on the deflecting mechanism to be in contact with a second magnet, positioned on the first longitudinal member, when the deflecting mechanism is in the first position.

2. The catheter of claim 1 further comprising one or more radiopaque markers disposed near the opening.

3. The catheter of claim 1, wherein the first or second region has a helical exterior.

4. The catheter of claim 1, wherein the first or second region comprises a plurality of wires.

5. The catheter of claim 4, wherein the plurality of wires comprise at least two different diameters.

6. The catheter of claim 4, wherein the plurality of wires are configured to be electrodes or conductive wires.

7. The catheter of claim 1, wherein the inner chamber is configured to receive a guidewire.

8. A recanalization system, comprising:
a guidewire; and
a redirecting delivery catheter comprising:
 a first longitudinal member having an inner chamber configured to receive the guidewire, an outer surface surrounding the inner chamber, a first region located at a proximal end, a second region located at a distal end, and a length;
 an opening in the outer surface extending along a portion of the length of the first longitudinal member between the first region and the second region;
 a deflecting mechanism located proximate to the opening and configured to be capable of transforming from a first position to a second position, wherein the deflecting mechanism is configured to enable the guidewire to access the second region when the deflecting mechanism is in the second position and to deflect the guidewire towards the opening when the deflecting mechanism is in the first position; and
 a support element coupled to the deflecting mechanism to support the deflecting mechanism in transforming from the first position to the second position, wherein the support element comprises one of a compressible circular ring configured to extend at least partially around the inner chamber when the deflecting mechanism is in the second position and to compress to a semicircular configuration when the deflecting mechanism is in the first position or a first magnet positioned on the deflecting mechanism to be in contact with a second magnet, positioned on the first longitudinal member, when the deflecting mechanism is in the first position.

9. The system of claim 8, wherein the guidewire comprises one or more electrodes.

10. The system of claim 8 further comprising a balloon catheter comprising one or more electrodes.

11. The system of claim 10, wherein at least one of the one or more electrodes is located inside the balloon catheter.

12. The system of claim 8, wherein the redirecting delivery catheter further comprises one or more radiopaque markers disposed near the opening.

13. The system of claim 8, wherein the first or second region has a helical exterior.

14. The system of claim 8, wherein the first or second region comprises a plurality of wires.

15. The system of claim 14, wherein the plurality of wires comprise at least two different diameters.

16. The system of claim 14, wherein the plurality of wires are configured to be electrodes or conductive wires.

17. A method of redirection of a guidewire, the method comprising:
inserting a guidewire into a vessel of a patient;
advancing a redirecting delivery catheter over the guidewire, the redirecting delivery catheter comprising:
 a first longitudinal member having an inner chamber configured to receive the guidewire, an outer surface surrounding the inner chamber, a first region located at a proximal end, a second region located at a distal end, and a length;
 an opening in the outer surface extending along a portion of the length of the first longitudinal member between the first region and the second region;
 a deflecting mechanism located proximate to the opening and configured to be capable of transforming from a first position to a second position, wherein the deflecting mechanism is configured to enable the guidewire to access the second region when the deflecting mechanism is in the second position and to deflect the guidewire toward the opening when the deflecting mechanism is in the first position, wherein the advancing positions the guidewire partially in the first region; and
 a support element coupled to the deflecting mechanism to support the deflecting mechanism in transforming from the first position to the second position, wherein the support element comprises one of a compressible circular ring configured to extend at least partially around the inner chamber when the deflecting mechanism is in the second position and to compress to a semicircular configuration when the deflecting mechanism is in the first position or a first magnet positioned on the deflecting mechanism to be in contact with a second magnet, positioned on the first longitudinal member, when the deflecting mechanism is in the first position;
retracting the guidewire into the first region to transform the deflecting mechanism from the second position to the first position;
advancing the guidewire toward the deflecting mechanism to redirect the guidewire toward the opening.

18. The method of claim 17, wherein the guidewire is redirected in a direction lateral to a distal opening of the redirecting delivery catheter.

19. The method of claim 18 further comprising applying energy from the guidewire to limit lateral force from the redirection of the guidewire.

20. The method of claim 18, wherein the guidewire comprises a 3-dimensional guidewire and advancing the 3-dimensional guidewire comprises rotating the 3-dimensional guidewire to limit lateral force from the redirection of the guidewire.

21. The method of claim 19, wherein the energy comprises radiofrequency, ultrasound, microwave, or laser.

22. The method of claim 17, wherein the guidewire is redirected to treat a bifurcation.

23. The method of claim 17 further comprising aligning the opening of the redirecting delivery catheter with a target area using one or more radiopaque markers located near the opening.

24. The method of claim 17, wherein the guidewire comprises a conductive electrode at a distal tip.

25. The method of claim 24 further comprising advancing a second conductive electrode to a position near the opening to create a bipolar arrangement between the conductive electrode at the distal tip and the second conductive electrode.

\* \* \* \* \*